US00PP23934P3

(12) United States Plant Patent
Larse

(10) Patent No.: US PP23,934 P3
(45) Date of Patent: Oct. 1, 2013

(54) STRAWBERRY PLANT NAMED 'GINZA'

(50) Latin Name: *Fragaria×ananassa*
Varietal Denomination: GINZA

(75) Inventor: John Larse, Aptos, CA (US)

(73) Assignee: Sweet Darling Sales Inc., Aptos, CA (US)

( * ) Notice: Subject to any disclaimer, the term of this patent is extended or adjusted under 35 U.S.C. 154(b) by 0 days.

(21) Appl. No.: 13/373,615

(22) Filed: Nov. 22, 2011

(65) Prior Publication Data

US 2013/0133115 P1 May 23, 2013

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Cooley LLP

(57) ABSTRACT

The present invention provides a new and distinct strawberry variety designated as 'Ginza' (a.k.a. '102011').

10 Drawing Sheets

Latin name of the genus and species: *Fragaria×ananassa.*
Varietal denomination: 'GINZA' (a.k.a. '102011').

BACKGROUND OF THE INVENTION

The present invention relates to a new and distinct day-neutral strawberry variety designated as 'GINZA' (a.k.a. '102011'). This new variety is the result of a controlled-cross between a female parent cultivar designated '1929' and a male parent cultivar designated '1902' (both unpatented, proprietary cultivars) made by the inventor and first fruited in Watsonville, Calif. growing fields.

Following selection and during testing, the plant was originally designated '102011' and subsequently named 'GINZA'. The new variety of 'GINZA' was asexually reproduced via runners (stolons) by the inventor at Watsonville, Calif. Asexual propagules from the original source have been tested in the Watsonville growing fields and, to a limited extent, growing fields in low and high elevation. The properties of this variety were found to be transmissible by such asexual reproduction. The cultivar is stable and reproduces true to type in successive generations of asexual reproduction.

SUMMARY OF THE INVENTION

This invention relates to a new and distinctive day-neutral type cultivar designated as 'GINZA'. It is primarily adapted to the climate and growing conditions of the central coast of California. This region provides the necessary temperatures required for it to produce a strong vigorous plant and to remain in fruit production from late-April through October. The nearby Pacific Ocean provides the needed humidity and moderate day temperatures and evening chilling to maintain fruit quality for the production months.

The following traits in combination distinguish strawberry variety 'GINZA' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

The following are the most outstanding and distinguishing characteristics of this new variety when grown under normal conditions in Watsonville, Calif.

Special shape, and

Petite size

The produced fruit is attractive and of excellent quality. Produced fruit is orange-red to medium-red at maturity, fruits are uniformly medium in size, firm, conical to oblate in shape with a smooth surface lacking creases. Seeds are well above the surface.

'GINZA' is primarily adapted to the growing conditions of the central coast of California, characterized by foliage small to medium in size and light to medium green in color. Production generally begins in April and produces continually into October with 40% to 50% of its production in the months of August through September.

'GINZA' is different from strawberry variety 'BOB', a.k.a. '105626' and strawberry variety 'ZARINA', a.k.a. '105218' disclosed in the co-pending applications. The table below shows differences among these varieties.

| Variety | 'BOB' (U.S. patent application No. 13/373,617) | 'GINZA' | 'ZARINA' (U.S. patent application No. 13/373,616) |
|---|---|---|---|
| Fruit Size | medium to large length: 4.2 cm width: 4.0 cm | uniformly medium in size length: 3.7 cm width: 3.6 cm | medium to large length: 4.4 cm width: 4.0 cm |
| Weight/Fruit | 20.7 g | 16.8 g | 25.6 g |
| Average weight/plant | 153.4 g | 91.7 g | 87.5 g |
| Average achenes/fruit | 251 | 220 | 271 |
| Fruit shape | mostly conical with some wedge | conical | Predominately conical |
| Surface Texture | smooth, lacking creases | smooth, lacking creases | smooth, lacking creases |
| Seed/Surface Position | Seeds are slightly sunken below the surface | Seeds are well above the surface | Seeds may be slightly sunken below the surface |

When 'GINZA' is compared to the proprietary female parent '1929', 'GINZA' is similar in proportion but lacks stolon yield.

When 'GINZA' is compared to the proprietary male parent '1902', 'GINZA' is smaller in size and fruit produced.

When 'GINZA' is compared to common variety 'Albion' (U.S. Plant Pat. No. 16,228), 'GINZA' is smaller in plant and fruit. Leaves are similar in length and width, however, but slightly denser. 'GINZA' has fruits that are smaller and more consistent in having a conical shape. Due to its proportions, 'GINZA' fruit is more resistant to weather variation.

DESCRIPTION OF THE DRAWINGS

The accompanying color photographs depict various characteristics of the 'GINZA' cultivar at various stages of development as nearly true as possible to make color reproductions.

FIG. 8 shows 'GINZA' after an early April shower.

DETAILED BOTANICAL DESCRIPTION

Figure 1:
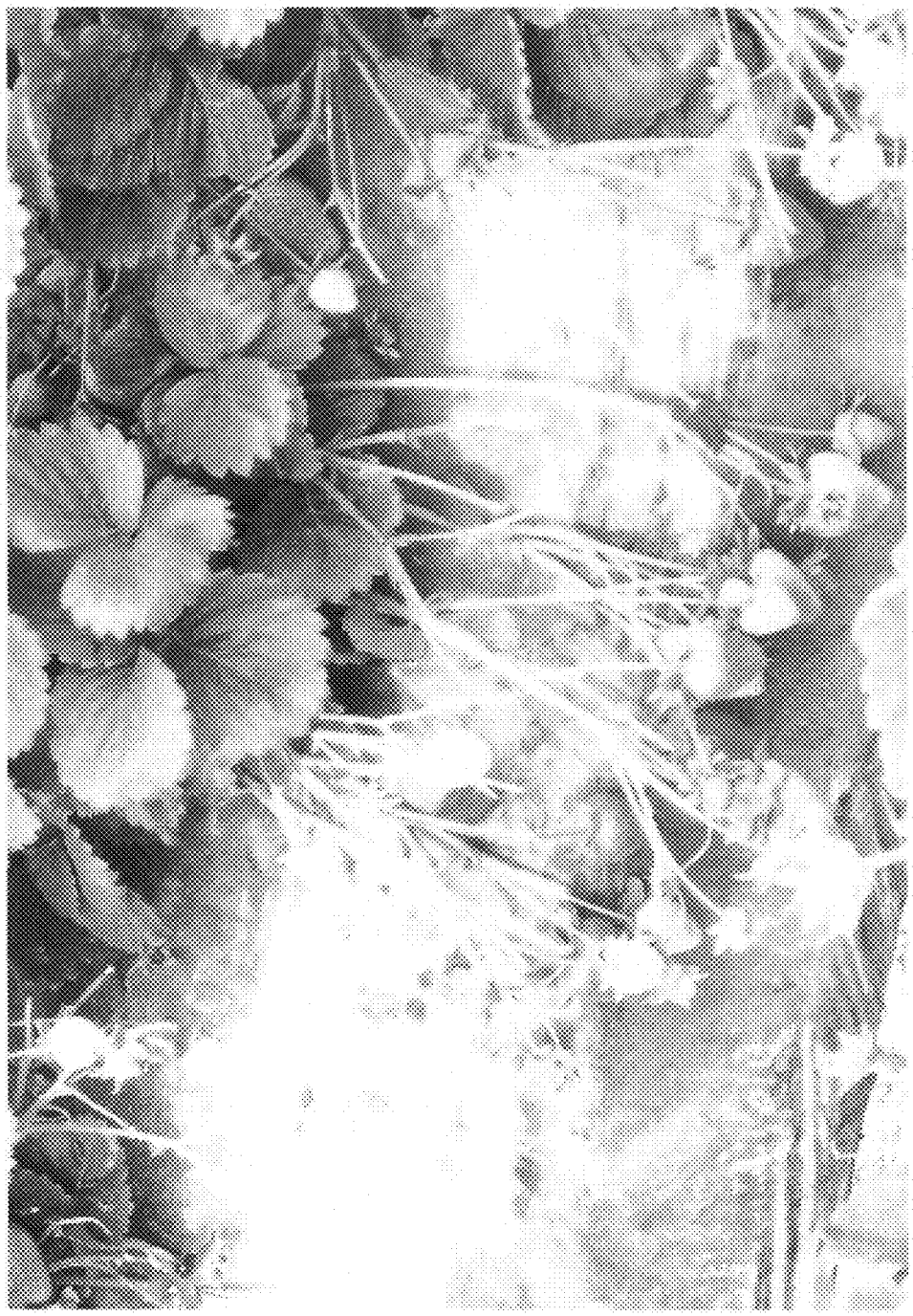
FIG. 1 shows the plant in its production stage bearing fruit.
Figure 2:
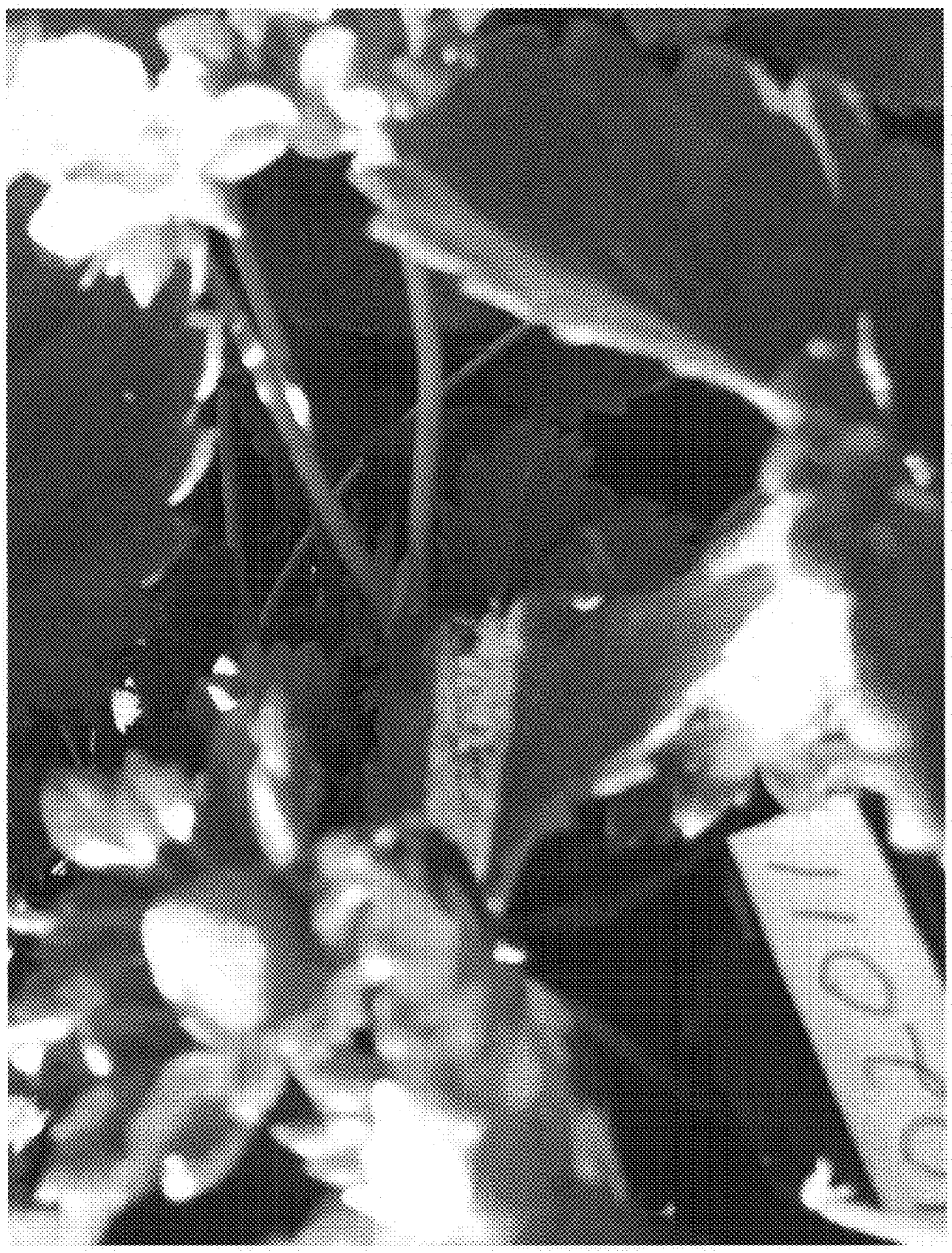
FIG. 2 shows the plant with flower and runners.
Figure 3:
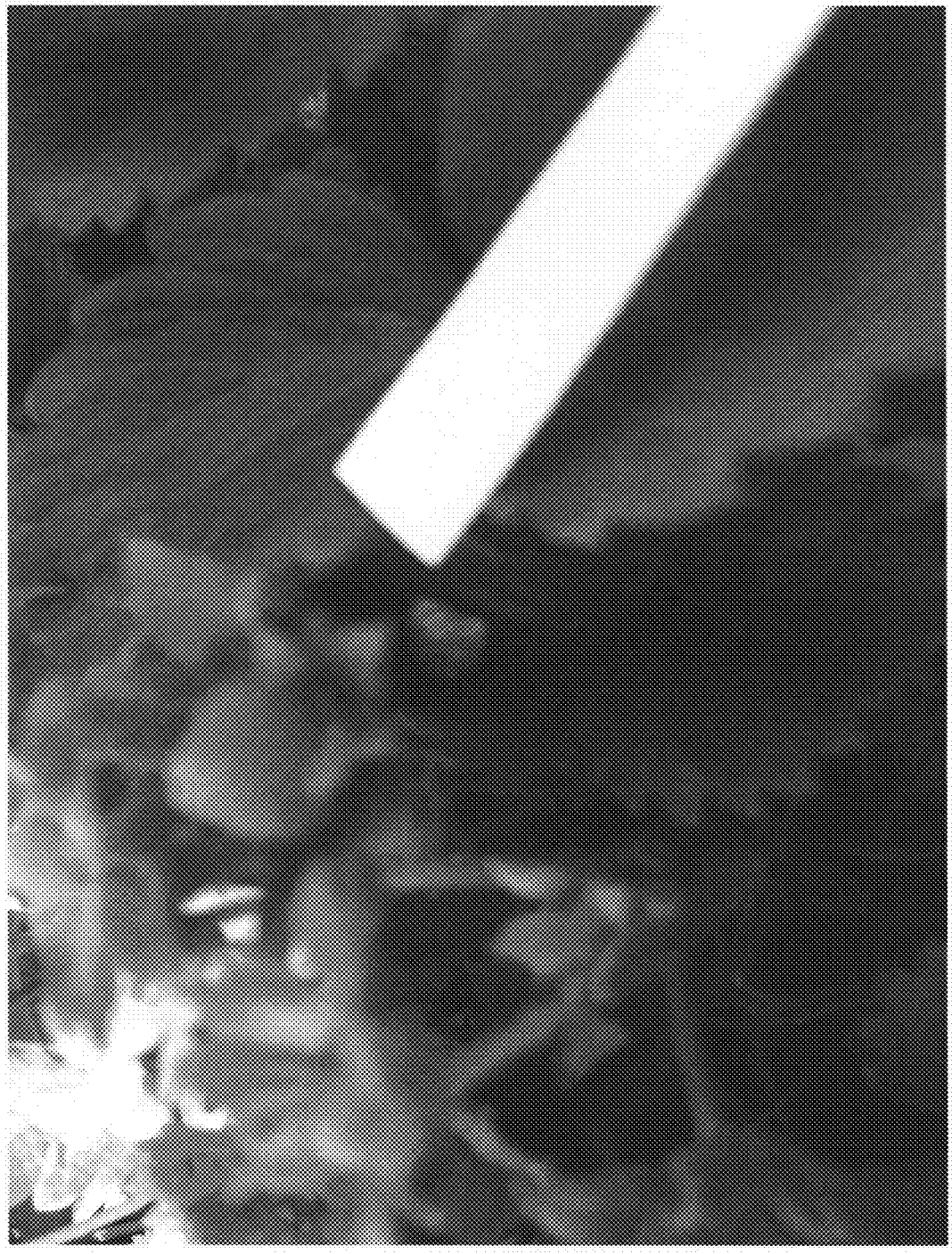
FIG. 3 shows typical leaves in the production cycle.
Figure 4:
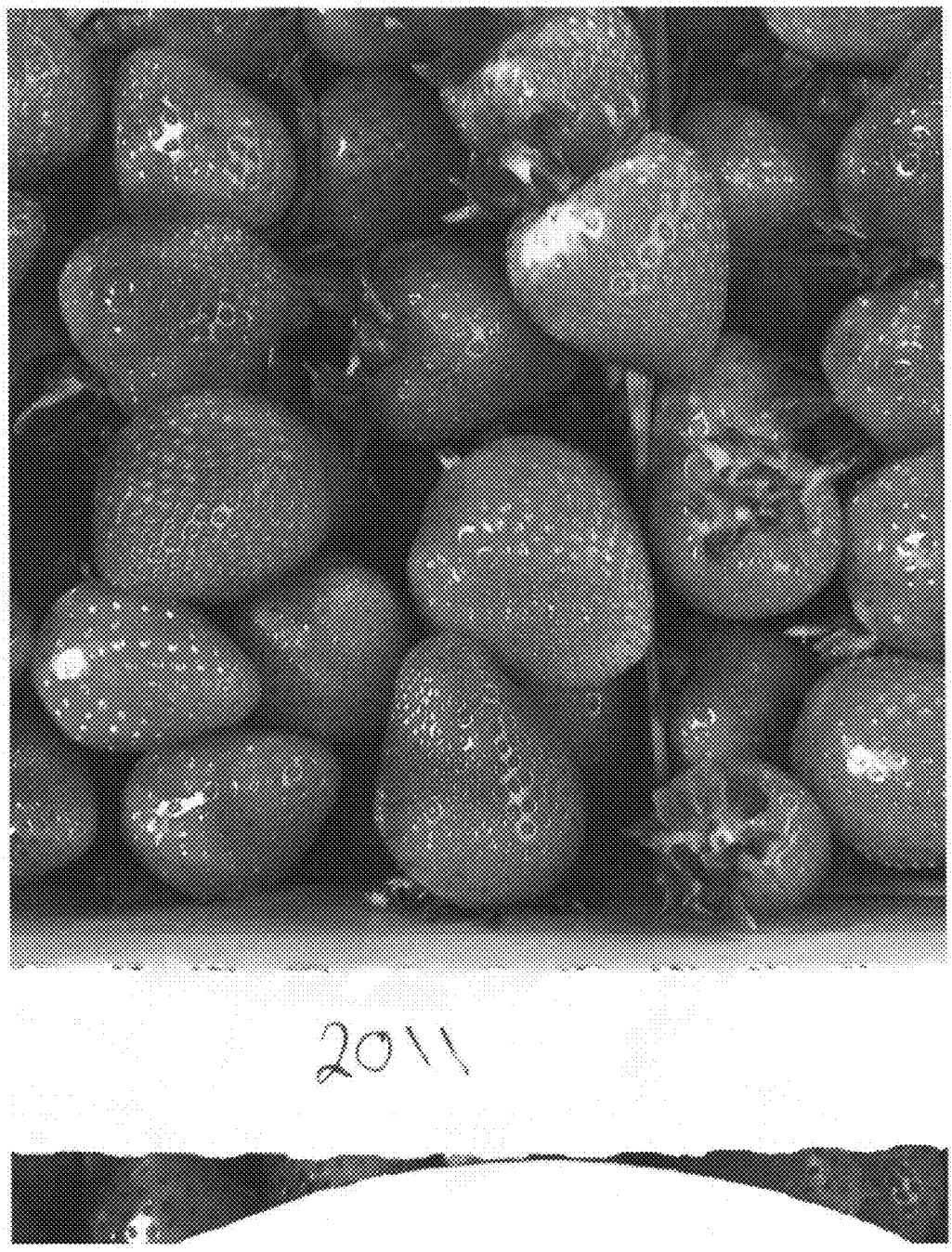
FIG. 4 shows ripe 'GINZA' fruit (October).
Figure 5:
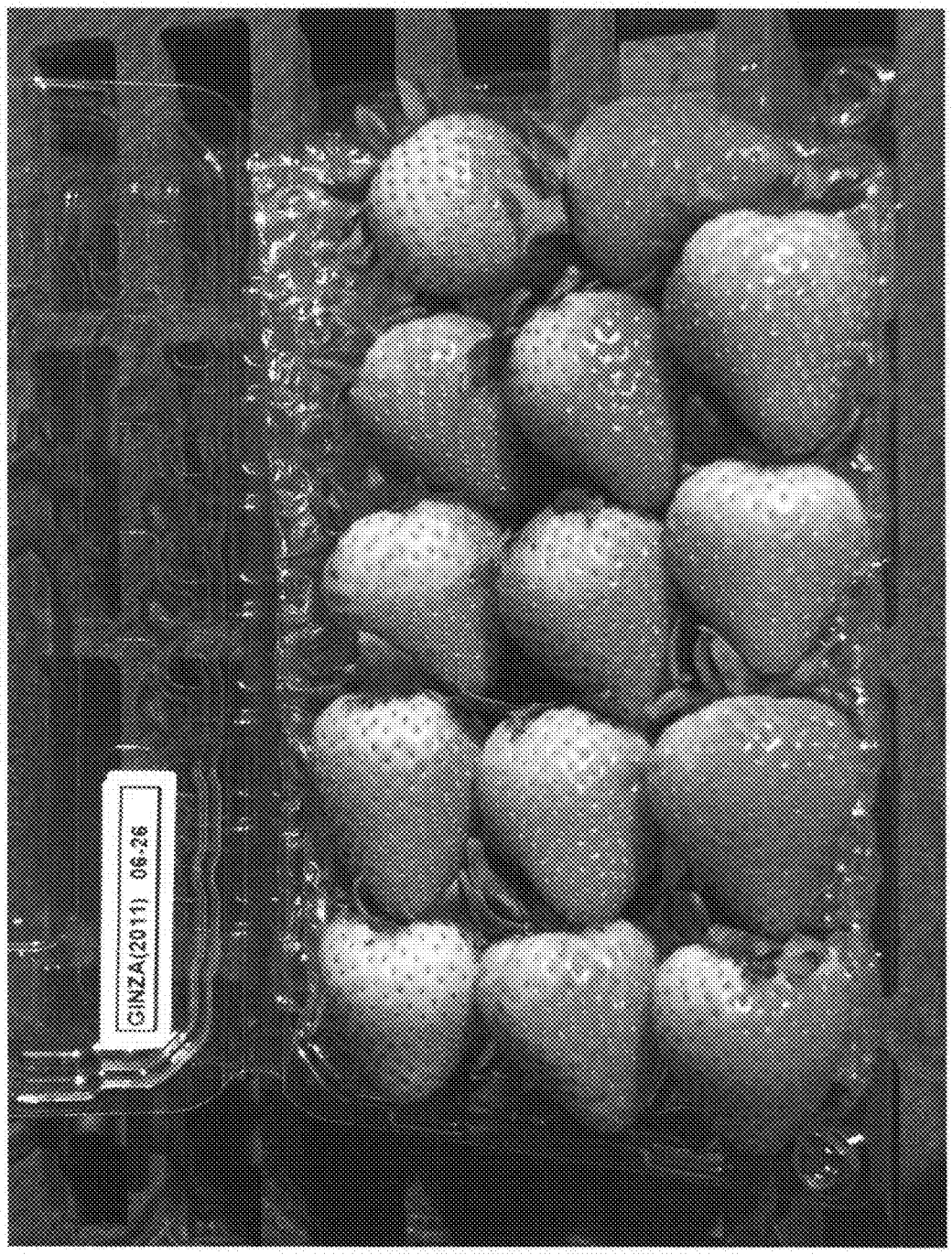
FIG. 5 shows ripe 'GINZA' fruit (June).
Figure 6:
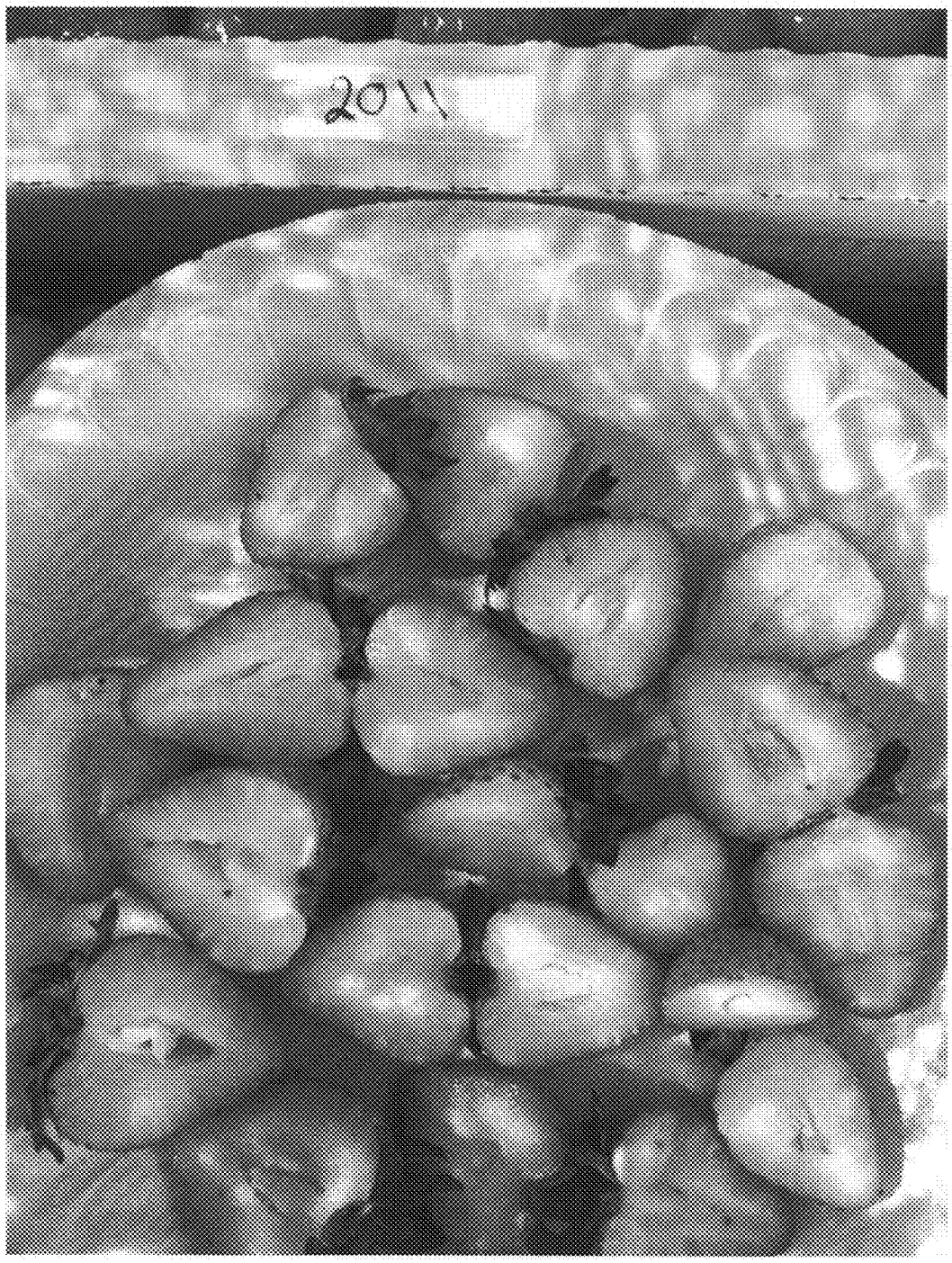
FIG. 6 shows sliced 'GINZA' fruit.
Figure 7:
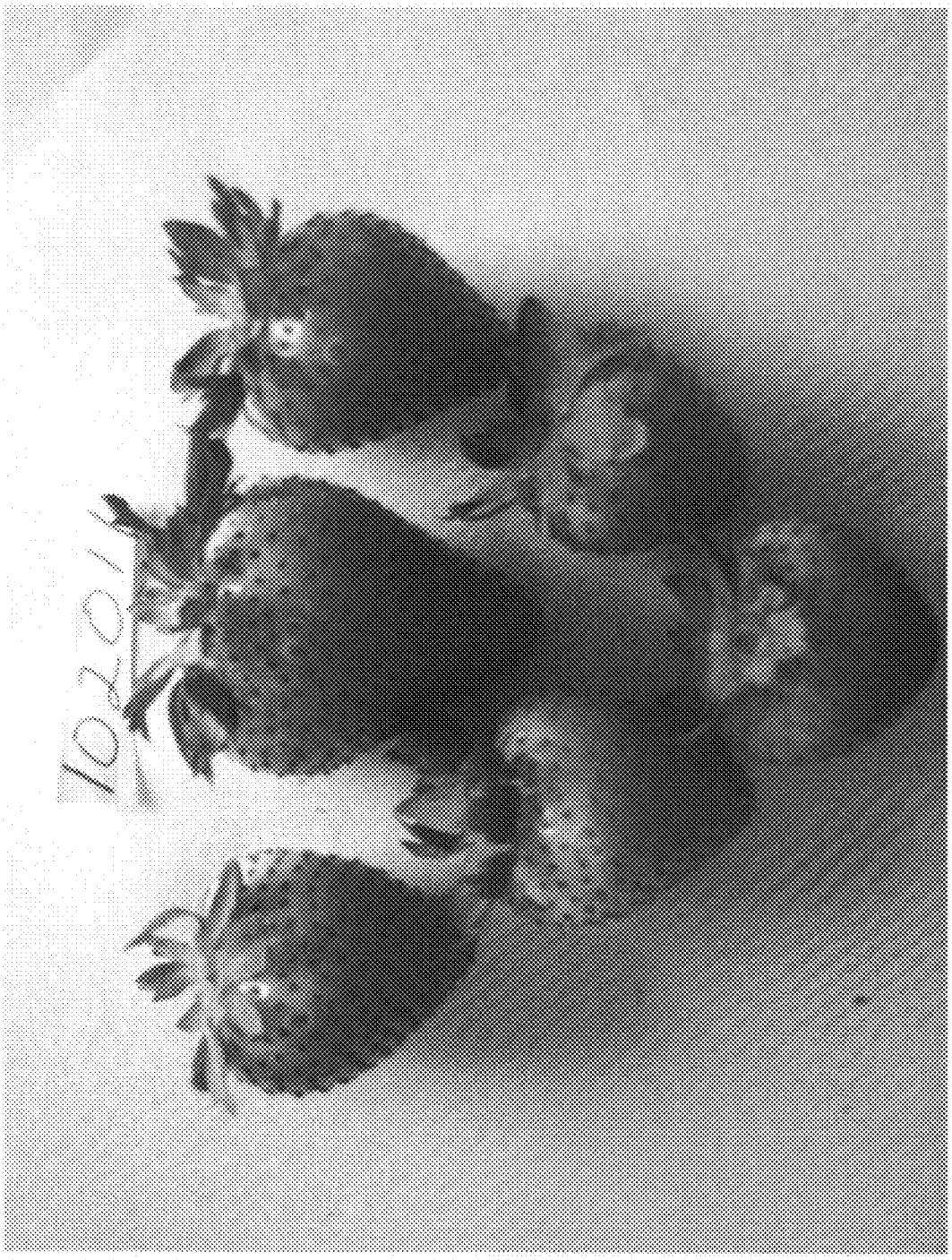
FIG. 7 shows ripe and near-ripe 'GINZA' fruits.
Figure 8:
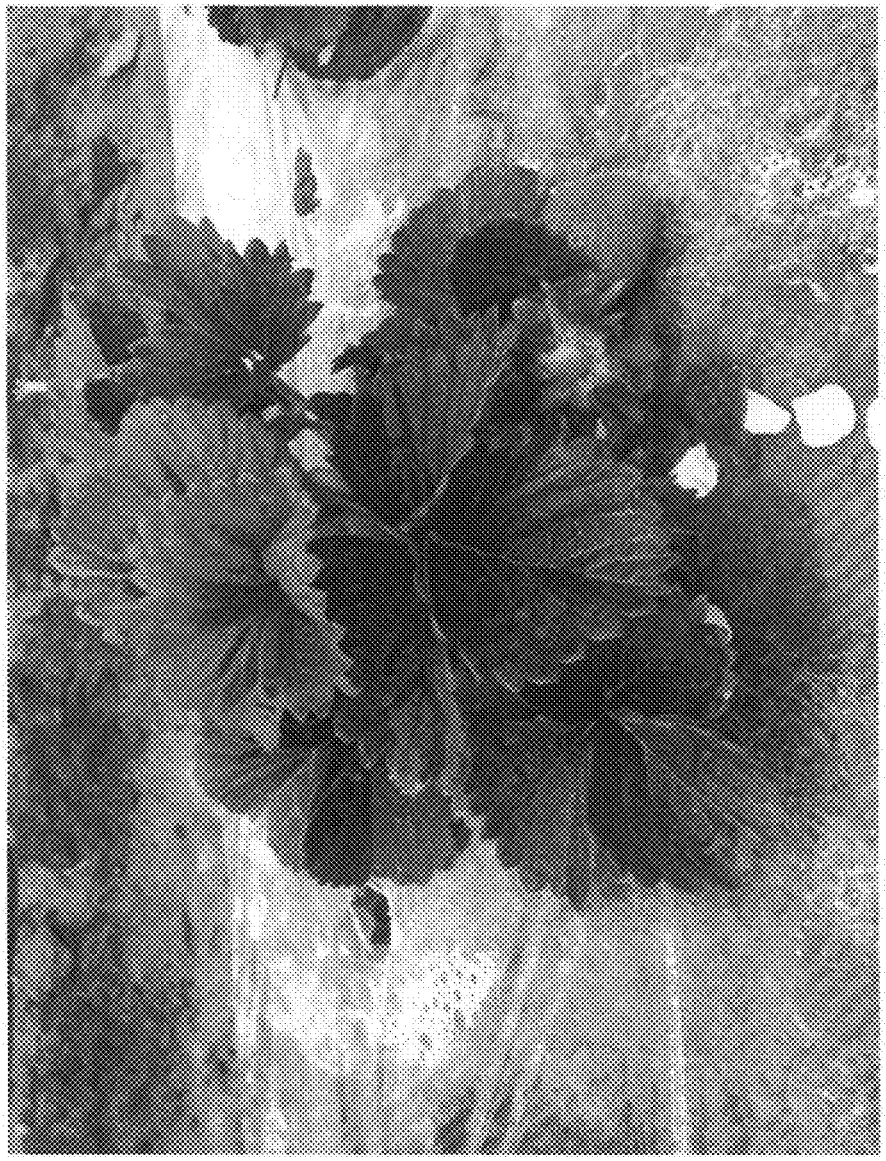
FIG. 8 shows 'GINZA' early in morning in late March.
Figure 9:
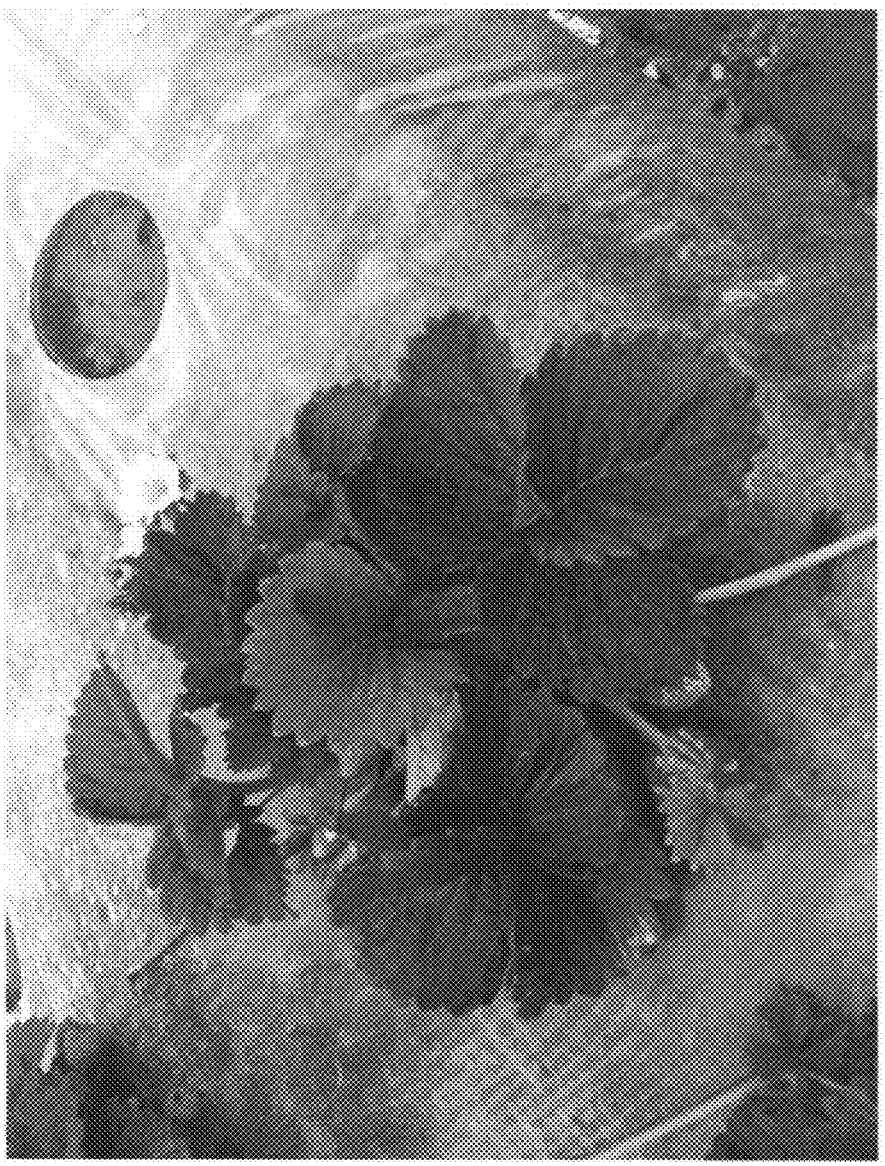
Figure 10:
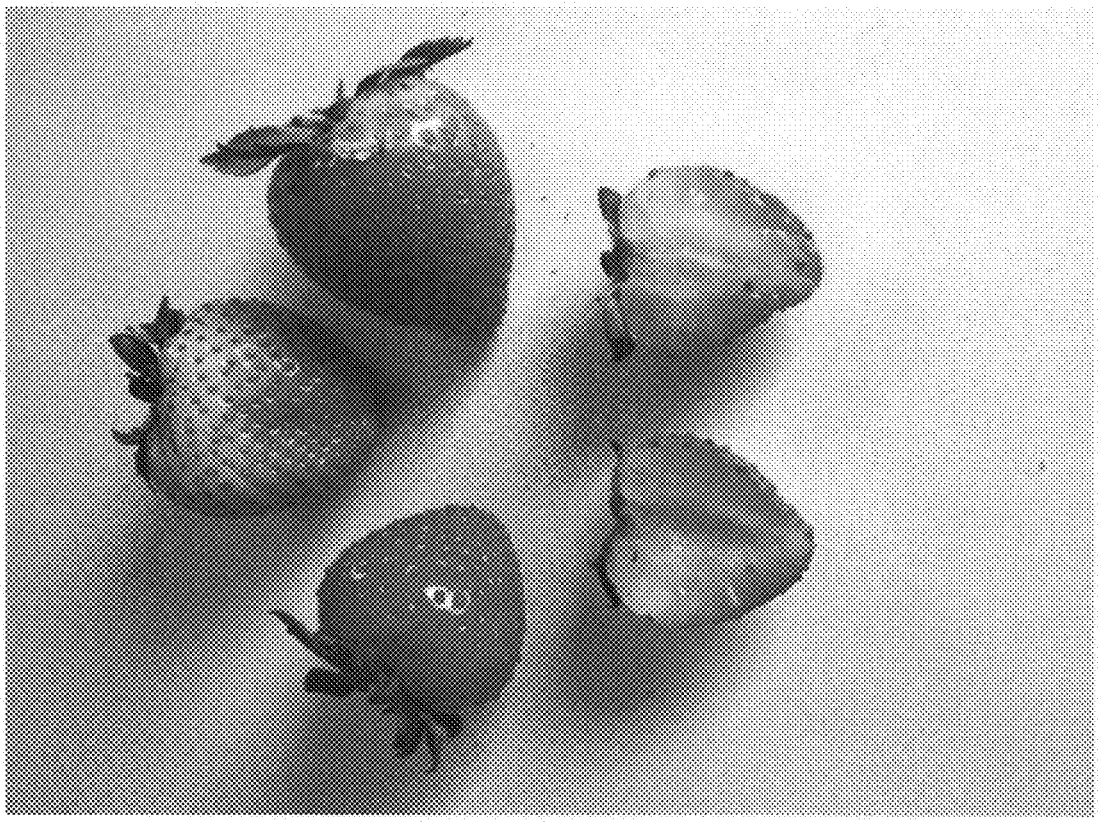
FIG. 10 shows 'GINZA' fruit from April.

This invention relates to a new and distinctive early-producing day-neutral (ever-bearing) type cultivar designated as 'GINZA', but may be considered a weak day-neutral in that it is somewhat similar to a short day. 'GINZA' is typical of day-neutral strawberry cultivars and produces fruit regardless of the day length when treated appropriately in moderate, coastal climates. 'GINZA''s fruit is uniformly medium in size, that is medium-firm to firm and conical to cylindrical or conical to oblate in shape with seeds above the surface; color is light orange or orange-red to medium red at maturity.

Among the characteristics that distinguish the new variety from the other closely related varieties are the timing of fruiting, plant vigor, position of the inflorescences, leaf morphology, leaf size, leaf density, leaf color, and disease and pest resistance.

'GINZA' has not been observed under all possible environmental conditions, and the phenotype may vary significantly with variations in environment. The following observations, measurements, and comparisons describe this plant as grown at California, when grown in the field, unless otherwise noted. As stated above, the color determination is in accordance with The Royal Horticultural Society Colour Chart, 1995 Edition, except where general color terms of ordinary dictionary significance are used. Plants for the botanical measurements in the present application are annual plants.

Botanical classification: 'GINZA' is a fertile hybrid derived from a cross.

Common name: Garden strawberry.

General description:

*Plant habit.*—Moderate, coastal climates.

The following description is applied to our plants that are about 4.5 months old as of the time of the measurements.

Classification:

*Species.*—*Fragaria×ananassa.*
*Common name.*—Garden Strawberry.
*Denomination.*—'GINZA'.

Parentage:

*Female parent.*—'1929'.
*Male parent.*—'1902'.

Plant:

*Height.*—13.3 cm.
*Diameter.*—16.8 cm.
*Habit.*—Globose, upright.
*Density.*—Medium.
*Vigor.*—Strong. Plant size is short to medium in stature. The shape of the base is obtuse and light to medium in density.

Terminal leaflet:

*Length.*—6.3 cm.
*Width.*—7.5 cm.
*Length/width ratio.*—0.8.
*Shape in cross-section.*—Concave.
*Blistering.*—Low.
*Glossiness.*—Medium.
*Average number of leaflets.*—Exactly 3.
*Color above.*—Dark Green (RHS 137A).
*Color below.*—Green (RHS 139C).
*Shape.*—Orbicular.
*Margin.*—Crenate to Serrate.
*Venation pattern.*—Reticulate. No bract leaves were observed in samples. The shape of the leaf is almost circular with the width slightly exceeding the length. The leaves are moderately to highly glossy. The shape of the leaves is slightly concave to almost flat.

Petiole:

*Length.*—6.3 cm.
*Width.*—4.6 mm.
*Color.*—Yellow Green (RHS 145A).

Petiolule:

*Length.*—10.4 cm.
*Width.*—2.2 mm.
*Color.*—Yellow Green (RHS 145A).

Stolon:

*Average daughters/plant.*—About 1.
*Diameter.*—3.6 mm.
*Color.*—Dark Purple Red (RHS 53A).

Inflorescence:

*Position relative to foliage.*—At same level.
*Average petals/flower.*—5.5.
*Petal length.*—13.7 mm.
*Petal width.*—13.3 mm.
*Petal length/width ratio.*—About 1.
*Petal shape/base.*—Orbicular.
*Petal apex.*—Round.
*Petal margin.*—Entire.
*Petal spacing.*—Slightly overlapping.
*Petal color.*—White (RHS 157B).
*Corolla.*—31.8 mm.
*Sepal length.*—13.2 mm.
*Sepal width.*—7.4 mm.
*Sepal length/width ratio.*—1.8.
*Sepal color.*—Dark Green (RHS 137A).
*Calyx.*—35.2 mm (Diameter relative to corolla: Larger).
*Peduncle.*—8.78 cm.

*Stipule frequency.*—Near Zero. The positioning of the inflorescence is predominately even with or above foliage. The flowers are mostly medium small to medium in size.

Fruit:

*Fruit truss attitude.*—Prostrate.
*Fruit/truss.*—1.
*Relative size.*—Large.
*Fruit length.*—3.7 cm.
*Fruit width.*—3.6 cm.
*Fruit length/width.*—About 1.
*Surface color.*—Red (RHS 45A).
*Flesh color.*—Orange Red (RHS 41B).
*Core color.*—White (RHS 155C).
*Shape.*—Conical.
*Average weight/fruit.*—16.8 g.
*Average weight/plant.*—91.7 g.
*Hollow core length.*—15 mm.
*Hollow core width.*—9 mm.
*Hollow core length/width ratio.*—1.7.
*Insertion of achenes.*—Prominently outside.
*Average achenes/fruit.*—220.
*Firmness of flesh.*—Firm.
*Glossiness.*—Medium.
*Sweetness.*—Medium. The plant produces mostly conical fruit with some long cones as well as long wedges and the fruit color is dull to light gloss. Seed position on fruit is somewhat indented. Fruit hardness was measured with a force dial and averaged 3.8 N to pierce the fruit 7.0 mm. The fruit's flavor is consistently good throughout the season.

Variety identification testing for 'GINZA': No matches to existing cultivars were found using SSR marker testing in a commercial database search.

It is claimed:

1. A new and distinct cultivar of strawberry plant named 'Ginza' substantially as shown and described herein.

* * * * *